(12) United States Patent
Ramirez-Vick

(10) Patent No.: US 7,108,971 B2
(45) Date of Patent: *Sep. 19, 2006

(54) REVERSIBLE BINDING OF MOLECULES TO METAL SUBSTRATES THROUGH AFFINITY INTERACTIONS

(75) Inventor: Jaime E. Ramirez-Vick, Berkeley, CA (US)

(73) Assignee: Iris Biotechnologies, Inc., Santa Clara, CA (US)

( * ) Notice: Subject to any disclaimer, the term of this patent is extended or adjusted under 35 U.S.C. 154(b) by 10 days.

This patent is subject to a terminal disclaimer.

(21) Appl. No.: 10/029,113

(22) Filed: Dec. 19, 2001

(65) Prior Publication Data

US 2004/0091858 A9    May 13, 2004

Related U.S. Application Data

(63) Continuation of application No. 09/571,084, filed on May 15, 2000, now abandoned.

(60) Provisional application No. 60/134,110, filed on May 14, 1999.

(51) Int. Cl.
*C12Q 1/68* (2006.01)
*C07H 21/04* (2006.01)

(52) U.S. Cl. ................. 435/6; 536/24.3; 536/24.33

(58) Field of Classification Search ............ 435/6, 435/91.1, 91.2, 16; 536/300, 23.1, 24.3, 536/24.33

See application file for complete search history.

(56) References Cited

U.S. PATENT DOCUMENTS

| | | | |
|---|---|---|---|
| 4,895,955 A | | 1/1990 | Ford et al. |
| 5,077,210 A | * | 12/1991 | Eigler et al. ................. 435/176 |
| 5,248,772 A | * | 9/1993 | Siiman et al. ............... 536/112 |
| 5,412,087 A | * | 5/1995 | McGall et al. ............. 536/24.3 |
| 5,465,151 A | * | 11/1995 | Wybourne et al. .......... 356/481 |
| 5,491,097 A | * | 2/1996 | Ribi et al. ................... 436/518 |
| 5,532,128 A | * | 7/1996 | Eggers et al. .................. 435/6 |
| 5,620,850 A | | 4/1997 | Bamdad et al. |
| 5,622,826 A | | 4/1997 | Varma |
| 5,622,828 A | | 4/1997 | Varma |
| 5,760,130 A | | 6/1998 | Johnston et al. |
| 5,837,860 A | | 11/1998 | Anderson et al. |
| 5,942,397 A | * | 8/1999 | Tarlov et al. .................. 435/6 |
| 5,985,548 A | * | 11/1999 | Collier et al. .................. 435/6 |
| 6,174,683 B1 | | 1/2001 | Hahn et al. |
| 6,197,515 B1 | | 3/2001 | Bamdad et al. |
| 6,500,609 B1 | | 12/2002 | Ribeill et al. |
| 6,613,508 B1 | | 9/2003 | Ness et al. |
| 2002/0009723 A1 | * | 1/2002 | Hefti ............................. 435/6 |

FOREIGN PATENT DOCUMENTS

| | | |
|---|---|---|
| WO | WO 96/18645 | 6/1996 |
| WO | WO 96/27680 | 9/1996 |
| WO | WO 99/20649 | 4/1999 |
| WO | WO 99/24645 | 5/1999 |
| WO | WO 99/42827 | 8/1999 |

OTHER PUBLICATIONS

Tomas A. Keller et al, "Reversible oriented immobilization of histidine-tagged proteins on gold surfaces using a chelator thioalkane", Supramolecular Science, GB, Oxford vol. 2, No. 3/ 04, 1995, pp. 155-160.

D J van den Heuvel et al., "Synthetic peptides as receptors in affinity sensors", Analytical Biochemistry, US, Academic Press, San Diego, CA vol. 215, No. 215, 1993, pp. 223-230.

Dr. R. Naumann et al., "Incorporation of membrane proteins in solid-supported lipid layers", Angewandte Chemie. International Edition, De Verlag Chemie. Weinheim, vol. 34, No. 18, 1995, pp. 2056-2058.

N. Bunjes et al., "Thiopeptide-supported lipid layers on solid surfaces", Langmuir, US, American Chemical Society, New York, NY, vol. 13, No. 13, Nov. 1997, pp. 6188-6194.

Perry-O'Keefe et al., "Peptide nucleic acid pre-gel hybridization: An alternative to Southern hybridization", Proc. Natl. Acad. Sci., vol. 93, pp. 14670-14675, Dec. 1996.

* cited by examiner

*Primary Examiner*—Young J. Kim
(74) *Attorney, Agent, or Firm*—Paul Davis; James A. Fox; Heller Ehrman LLP

(57) ABSTRACT

This invention is related to methods for the immobilization of labeled ligands on solid surfaces using soft metal-soft base bonding. The ligand-binding solid surface comprises a soft metal solid support and a heterobifunctional spacer chemi- or physisorbed to said soft metal solid support via soft metal-soft base bonding.

13 Claims, 3 Drawing Sheets

Soft metal surface →

Succinimidyl-6-(biotinamido)hexaonate

Phosphoramidate labeled oligonucleotide

Soft metal surface

Dithio-bis(succinimidylundecanoate)

Amino-labeled PCR product

Soft metal surface

Succinimidyl 6-[6-(((iodoacetyl)amino)-hexanoyl)amino]hexaonate

Antibody with available amino groups

REVERSIBLE BINDING OF MOLECULES TO METAL SUBSTRATES THROUGH AFFINITY INTERACTIONS

This is a continuation of pending prior application Ser. No. 09/571,084, filed May 15, 2000, now abandoned, which application claims the benefit under 35 U.S.C. 119(e) of U.S. Provisional Application Ser. No. 60/134,110, filed May 14, 1999.

BACKGROUND OF THE INVENTION a) Field of the Invention

This invention is related to immobilization of ligands onto solid surfaces and their use in hybridization, purification, immunoassays, biosensors, and other biochemical applications.

b) Description of Related Art

Solid supports for the immobilization of ligands, such as nucleotides, proteins, enzymes, and cells, are extensively used in hybridization, purification, immunoassays, and many other biochemical applications.

U.S. Pat. No. 5,622,826, issued Apr. 22, 1997, discloses a method by which amino-labeled oligonucleotides are immobilized onto glass by using an isocyanate linker, particularly 1,3-phenylene diisocyanate. This approach suffers from the limitation that 1,3-phenylene diisocyanate is reactive to both hydroxyl and thiol groups, thus lowering dramatically the specificity of the molecule. Further, 1,3-phenylene diisocyanate is a small, inflexible molecule which binds the ligand close to the surface.

Cohen et al. (*Nucleic Acids Res.*, 1997, 25(4), 911–912) disclose a method for immobilizing oligonucleotides to glass using phosphite-triester chemistry for solid phase oligonucleotide synthesis. The phosphite-triester molecules bind multiple hydroxyl groups on the glass surface and the phosphate group at the 5'-end of the nucleotide. Although this approach provides a stable covalent bond to the surface, it has the limitations of binding the ligand close to the surface, thus lowering the exposure of the ligand, as well as occupying three hydroxyl groups per ligand, thus lowering the surface density of ligand.

Alkylsiloxanes are one of the most widely used classes of molecules for activating glass surfaces with functional groups (Weetall, H. H., *Appl. Biochem. Biotechnol.*, 1993, 41, 157–188). These molecules form self-assembled monolayers (SAMs) when the reactive siloxane group condenses with hydroxyl groups of the surface and neighboring siloxanes to form a crosslinked network (Mrksich, M., and Whitesides, G. M., *Annu. Rev. Biophys. Biomol. Struct.*, 1996, 25, 55–78).

In U.S. Pat. No. 5,837,860, issued Nov. 17, 1998, Anderson and Rogers disclose a method of immobilize single nucleic acids or oligonucleotides labeled with terminal sulfhydryl or disulfide functional groups. Mercaptosilane molecules are first immobilized onto a glass or polystyrene solid surface to which the labeled nucleotides form a covalent disulfide bond, using mercaptoethanol or dithiothreitol as reducing agents.

In U.S. Pat. No. 5,760,130, issued Jun. 2, 1998, Johnston and Trounstine disclose a method for immobilizing DNA using aminoalkylsilanes. After the aminoalkylsilanes are immobilized on the glass surface, a carbodiimide solution in an imidazole buffer forms an intermediate that reacts with the phosphate group at the 5'-end of DNA. Lom, B., et al., *J. Neurosci. Meth.*, 1993, 50, 385–397 used alkylsiloxanes with a mixture of amino and alkane functionalities to bind proteins by interacting with their hydrophilic and hydrophobic moieties. Others have used alkylsiloxanes functionalized with iodine, benzyl chloride, and epoxide to interact with amino and thiol groups of antibodies (Pope, N. M., et al., *Bioconj. Chem.*, 1993, 4(2), 166–171). Maskos and Southern (*Nucleic Acids Res.*, 1992, 20(7), 1679–1684) used epoxy alkylsilanes and ethylene glycol derivatives to immobilize nucleotides for solid phase synthesis. The epoxy alkylsilanes serve as spacers, while the ethylene glycol derivatives provide hydroxyl groups that are oxidized to react with the phosphate group at the 5'-end of the nucleotide.

Aminoalkylsiloxanes have also been used to immobilize DNA lengthwise on glass surfaces (Yokota et al., *Nucleic Acids Res.*, 1997, 25(5), 1064–1070). The mechanism by which the aminated surface binds DNA is not clear, but is thought to be based on electrostatic interactions. This interaction is far from specific since these aminated surfaces are able to bind any nucleotide sequence. Also, the strength of the interaction is weak, since, after binding, the DNA is straightened by spreading the liquid on the glass surface.

One problem with the use of alkylsiloxanes is that they do not necessarily form SAMs as originally thought (Vandenberg, et al., *J. Colloid Inter. Sci.*, 1991, 147(1), 103–118). Instead of an ordered well-defined structure, they may form aggregates on the surface, thus lowering the surface binding capacity. The structure which alkylsiloxanes form on the glass surface is highly dependent on the reaction conditions.

Another approach for binding DNA lengthwise (or at least at various points across its length) on a glass surface uses poly-1-lysine (Schena, et al., *Science*, 1995, 270, 467–470, and Shalon, et al., *Genome Res.*, 1996, 6, 639–645). As with the use of aminoalkylsiloxanes, this interaction is not specific and thus weak, resulting in loss of ligand if stringent washing steps are needed.

The interaction of metal ions with specific amino acids on the surface of proteins was first used by Porath et al. (*Nature*, 1975, 258, 598–607) in chromatography to separate serum proteins using metal ions immobilized by imidoacetate. Following this, most binding studies using metal ions have relied on transition metal ions (e.g., Cu(II), Ni(II), Fe(III), and Zn(II)) which interact with indole and imidazole groups present in proteins.

In U.S. Pat. No. 5,620,850, issued on Apr. 15, 1997, Bamdad et al. attached a construct of a long chain hydroxyalkylthiol and a Ni(II) chelator to a gold surface. Ni(II) is a transition metal ion, which interacts with functional groups present in proteins.

The work by Garcia and co-workers has demonstrated that the soft metal acids Ag(I) and Pt(II) can be used to immobilize proteins and oligonucleotides. Immobilized silver ions have been demonstrated to provide a unique affinity series in the chromatographic separation of amino acids (García, A. A., et al., *Reactive Polymers*, 1994, 23, 249–259) and a preference of biotin labeled BSA over its unlabeled counterpart (García, A. A., et al., *Ind. Eng. Chem. Res.*, 1996, 35(4), 1097–1106). Also, a biotin labeled nucleotide (b-dUTP) was shown to be retained through affinity interactions, while dUTP was not retained on an immobilized silver ion column when the sodium chloride concentration exceeded 0.001 M (Agarwal, et al., *Sep. Sci. Technol.*, 1998, 33(1), 1–18). Silver ions have also been immobilized onto colloidal paramagnetic particles in order to recover biotin-labeled oligonucleotides from a mixed population (Ramírez-Vick, J. E., and García, A. A., *Reactive and Functional Polymers*, 1998, 35,123–132).

The use of soft metal ions as anchor groups has been demonstrated when the protein clathrin was immobilized onto a gold surface by using NHS ester-activated dodecanethiols (Wagner, et al., *FEBS Letters*, 1994, 356, 267–271).

In U.S. Pat. No. 5,622,826, issued on Apr. 22, 1997, Vanna discloses a method for using platinum wafers as a solid surface for immobilizing amino-labeled oligonucleotides, using 1,4-phenylene diisothiocyanate. This molecule lacks the flexibility necessary to be able to bind the labeled ligand at a high surface density while providing the necessary availability to bind the maximum amount of receptor biomolecule possible.

The object of the present invention is to provide an improved method for the immobilization of labeled ligands onto solid surfaces. Several longstanding problems in hybridization, purification, immunoassays, biosensors, and other biochemical applications are resolved by this invention.

SUMMARY OF THE INVENTION

This invention provides a ligand-binding solid support having a soft metal solid surface and a heterobifunctional spacer chemi- or physisorbed to the soft metal solid surface via soft metal-soft base bonding. Preferably the soft metal solid surface is silver, copper, gold, platinum (II), mercury, mercury (II), thallium, cadmium (II), platinum (IV) or palladium (II). The heterobifunctional spacer is preferably a hydrocarbon of chain length from about 10 to about 40 carbon atoms, having at least one soft base anchor group and at least one nucleotide binding group. The soft base anchor group is an RSH, RS$^-$, R$_2$S, RSSR, CN$^-$, S$_2$O$_3^{2-}$, I$^-$, R$_3$P, (RO)$_3$P, C2H4 or C6H6 group, where R is an organic group. Optionally, an oligonucleotide is pre-attached to the spacer.

This invention also provides methods for preparing a ligand-binding solid surface, by selecting a soft metal solid surface and immobilizing a heterobifunctional spacer on said solid surface via soft metal-soft base bonding.

Assay systems having soft metal solid surfaces and a heterobifunctional spacer chemi- or physisorbed to said soft metal solid surface via soft metal-soft base bonding are also provided, as are methods for detecting the presence of a biological molecule by exposing a sample containing biological molecules to a surface as defined above.

DETAILED DESCRIPTION OF THE INVENTION

I. Definitions

Figure 1:
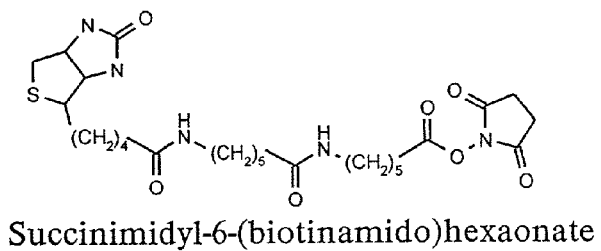
FIG. 1 shows the basic process of activation of a soft metal surface in order to immobilize amino-labeled oligonucleotides.
Figure 1:
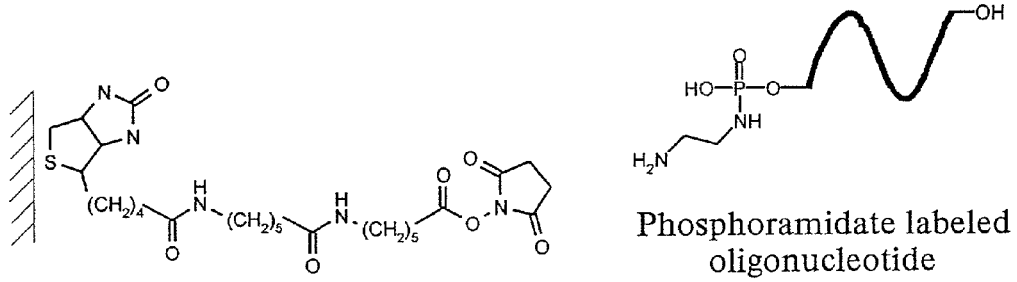
Figure 1:
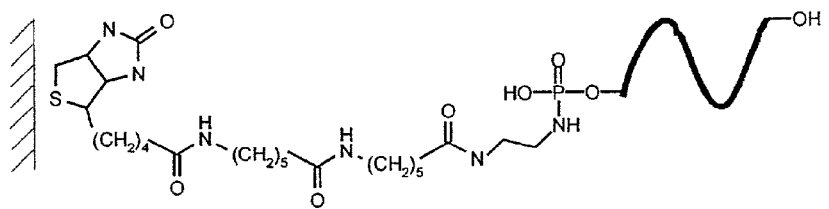
Figure 2:
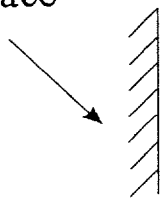
FIG. 2 shows the basic process of activation of a soft metal surface in order to immobilize amino-labeled cDNAs.
Figure 2:
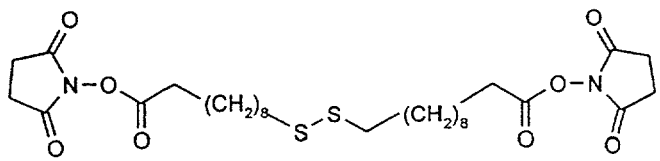
Figure 2:
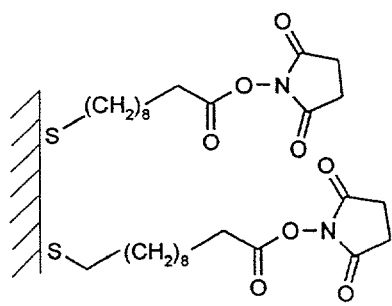
Figure 2:
Figure 2:
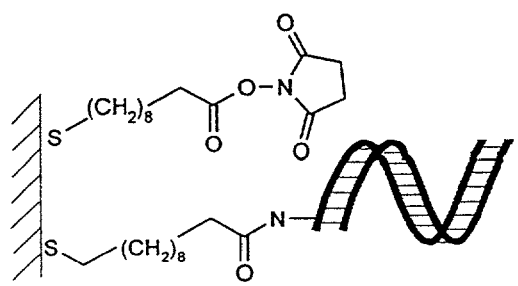
Figure 3:
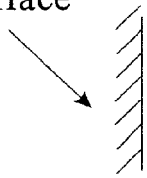
FIG. 3 shows the basic process of activation of a soft metal surface in order to immobilize amino-labeled antibodies.
Figure 3:
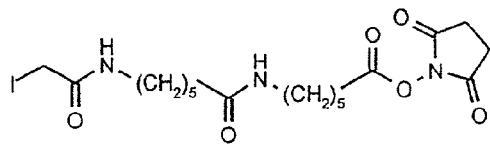
Figure 3:
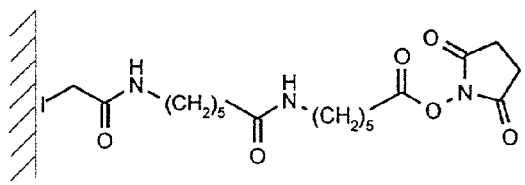
Figure 3:
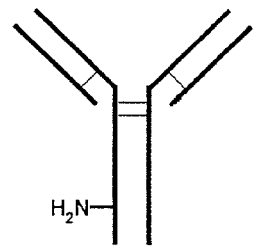
Figure 3:
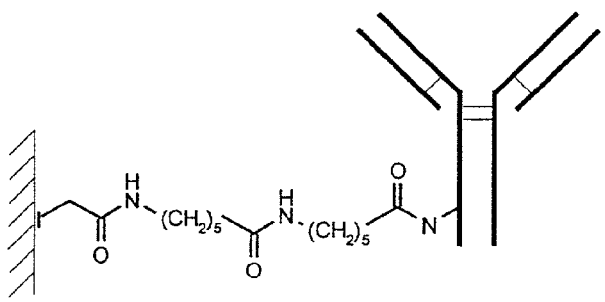

Unless indicated otherwise, the terms defined below have the following meanings:

"Anchor group" refers to the functional chemical group containing the soft base that sorbs the spacer to the soft metal surface.

"Binding density" refers to the number of reactive terminal groups per unit surface area available for binding the labeled biopolymer.

"Biopolymer" refers to biological molecules such as proteins, oligonucleotides, DNA, etc., which are the basis of hybridization, purification, immunoassays, and many other biochemical applications.

"Hybridization" refers to binding reaction between complementary partners of biopolymer molecules.

"Ligand" refers to one member of the ligand/receptor binding pair, such as, oligonucleotides, DNA, and proteins.

"Nonspecific interaction" refers to the individual physico-chemical interactions (i.e., hydrogen bonds, ionic bonds, hydrophobic interactions, and van der Waals forces) where structure is not involved.

"Protein" refers to enzymes, antibodies, and any other polypeptides.

"Soft bases" refer to the species defined as having a small charge and large size and preferring to bind with soft metals.

"Soft metals" refer to the species defined as having a small charge and large size and preferring to bind with soft bases.

"Spacer arm" refers to the molecule that helps make the immobilized ligand flexible enough to make it accessible to the receptor. This is usually a long chain hydrocarbon, optionally containing heteroatoms, and having at least two functional groups.

"Specific interactions" refers to the sum total of a particular set of physico-chemical interactions where structure can play a major role. These interactions include hydrogen bonds, ionic bonds, hydrophobic interactions, and van der Waals forces.

"Steric hindrance" refers to the effect by large groups near the ligand, which limits its accessibility to the receptor molecule.

II. Immobilization of Molecules on Soft Metal Surfaces

This invention is related to the immobilization of labeled ligands onto solid surfaces using soft metal-soft base binding. This invention provides processes for the development of reliable techniques for immobilizing biologically active biopolymer probe molecules, obtaining high sensitivity and high selectivity, and at lower cost through reuse of sensing elements.

The general process involves the use of substrates containing soft metal thin films. Heterobifunctional spacer molecules are then added. This heterobifunctional spacer is a hydrocarbon having a chain length of about 10 to about 40 carbon atoms, preferably about 15 to about 25 carbon atoms, having at least two functional groups. Of the two functional groups, one is a soft base that will sorb with the soft metal surface. The other functional group on the spacer is selected to bind the functional group on the label of the ligand. Optionally, an oligonucleotide is pre-attached to the spacer prior to sorption on the metal surface. This process creates an active solid surface that is able to bind labeled ligands in high density and with minimum nonspecific binding.

The (anchor group-spacer arm-reactive terminal moiety) structure provides a stable anchor bond to the solid surface, a spacer arm which gives flexibility to the ligand allowing it to interact with its environment in a way which minimizes any steric hindrance, and a reactive terminal moiety which binds the ligand. Optionally, an oligonucleotide may serve as the reactive terminal moiety. The choice of the individual components of this immobilization structure depends on the combination that provides a minimum in nonspecific interactions and steric hindrance, and a maximum in binding density. The type of anchor group used will provide the solid support with the proper functionality to immobilize a spacer arm with a reactive terminal group. This immobilization structure can either be built piecemeal upon the solid substrate or pre-assembled and sorbed as one unit to the surface. The soft base anchor group is an RSH, RS$^-$, R$_2$S, RSSR, CN$^-$, S$_2$O$_3^{2-}$, I$^-$, R$_3$P, (RO)$_3$P, C2H4 or C6H6 group, where R is an organic group.

The present invention also provides methods for immobilizing oligonucleotides labeled with amino groups onto soft metal surfaces activated with a biotin-NHS ester heterobifunctional spacer arm.

The present invention also provides methods for immobilizing cDNA or PCR-amplified DNA labeled with amino groups onto soft metal surfaces activated with an iodine-NHS ester heterobifunctional spacer arm.

The present invention also provides methods for immobilizing proteins onto soft metal surfaces activated with a sulfhydryl-NHS ester heterobifunctional spacer arm.

The present invention also provides methods for recovering the immobilized ligands by using sulfur-containing competing molecules to displace the heterobifunctional spacers. Due to the high aqueous solubility of thiodiglycol and its thioether functional group, a high elution recovery can be accomplished using a concentrated solution of thiodiglycol. The substrate may then be reused by washing with water and ethanol followed by heating under a partial vacuum in order to drive off the relatively volatile thiodiglycol.

The sorbed molecules are bound to the solid surface by valence forces similar in strength to those involved in covalent bonds. However, unlike covalent interactions, there is a dynamic equilibrium in which adsorbed molecules can be desorbed without breaking any bonds. The interaction between soft metal ions and soft bases is described qualitatively by the principle of Hard and Soft Acids and Bases (HSAB) based on the Lewis definition of acids and bases (Pearson, R. G., Chem. Brit. 1967, 3, 103–107. Pearson, R. G., J. Chem. Ed. 1968, 45, 581–587. Pearson, R. G., J. Chem. Ed. 1968, 45, 643–648). This principle states simply that hard acids prefer to coordinate with hard bases and soft acids with soft bases. It defines hard acids as those that are small in size, of high positive charge, and do not contain unshared pairs of electrons in their valence shell. These properties lead to high electronegativity and low polarizability. Soft acids are large in size, of low positive charge, and containing unshared pairs of electrons (p or d) in their valence shell. This leads to high polarizability and low electronegativity. Thus soft acids form stable complexes with bases that are highly polarizable. While hard acids, of which the proton is typical, will usually form stable complexes with bases such that polarizability plays only a minor role. Acids and bases can thus be classified according to these premises into hard, soft, or borderline (TABLE 1). Since these acid/base interactions comprise a number of different properties, there is also more than one theory which describe them. These theories are the ionic-covalent, the π-bonding, and the electron correlation theories.

TABLE 1

CLASSIFICATION OF LEWIS ACIDS AND BASES

| Class | Acids | Bases¶ |
|---|---|---|
| Hard | H, Li, Na, K, Be$^2$, Mg$^2$, Ca$^2$, Sr$^2$, Fe$^3$ | H$_2$O, OH—, F—, Cl—, CH$_3$COO—, SO$_4^{2-}$—, NO$_3$—, ROH, RO—, NH$_3$, RNH$_2$ |

TABLE 1-continued

CLASSIFICATION OF LEWIS ACIDS AND BASES

| Class | Acids | Bases¶ |
|---|---|---|
| Borderline | Cu$^2$, Zn$^2$, Ni$^2$, Fe$^2$, Co$^2$, Pb$^2$, Sn$^2$, Sb$^3$ | C$_6$H$_5$NH$_2$, C$_5$H$_5$N, N$_3$—, Br—, NO$_2$—, SO$_3^{2-}$— |
| Soft | Ag, Cu, Au, Pt$^2$, Hg, Hg$^2$, Tl, Cd$^2$, Pt$^4$, Pd$^2$ | RSH, RS—, R$_2$S, CH—, S$_2$O$_3^{2-}$—, I—, R$_3$P, (RO)$_3$P, C$_2$H$_4$, C$_6$H$_6$ |

¶R stands for alkyl group, e.g., CH$_3$, C$_2$H$_5$, etc.

The ionic-covalent theory is the oldest and the most obvious. It states that hard acids interact with hard bases mainly by ionic forces because of their small size and high charge. Soft acids and bases with their large size and small charge cannot form a stable complex through ionic forces. The π-bonding theory states that soft acids (usually metals) with loosely held d-orbital electrons can form π bonds with soft bases that contain empty d-orbitals. Finally, the electron correlation theory suggests that London or Van der Waals dispersion energies between atoms or groups in the same molecule may lead to the stabilization of the molecule. These forces are large in complexes formed by highly polarizable soft acids and bases, thus providing additional stability.

The various methodologies mentioned in this disclosure are well-known to those skilled in the art. Such methodologies can be found in standard references such as: Hermanson, G. T., Bioconjugate Techniques, 1996, Academic Press, San Diego, Calif.; Birren, B., et al., Genome Analysis: A Laboratory Manual, 1995, Cold Spring Harbor Laboratory Press, Cold Spring Harbor, N.Y.

The first step in the immobilization process is the fabrication of soft metal thin films (about 20 nm) on the substrate of choice (e.g., fused silica, lime glass, quartz, oxidized silicon, etc.). This is done by well known methods such as electron beam evaporation.

After washing and drying, the heterobifunctional spacer arm is absorbed. Various types of heterobifunctional spacers are commercially available or protocols for their synthesis can be found in the literature. Of the different functional groups in the spacer at least one is a soft base to bind the soft metal surface. One other functional group is reactive towards the ligands or biomolecules to be immobilized. All of these chemical groups and reactions are well known to those skilled in the art and some examples are shown in TABLE 2.

TABLE 2

REACTIVE CHEMICAL GROUPS

| Functional Group | Reactive Group |
|---|---|
| Amino | Isothiocyanates |
|  | Isocyanates |
|  | NHS esters |
|  | Carbodiimides |
| Thiol | Haloacetyl derivatives |
|  | Maleimides |
|  | Disulfide reductants |
| Carboxylate | Carbonyldiimidazole |
|  | Carbodiimides |
| Hydroxyl | Epoxides |
|  | Carbonyldiimidazole |
|  | Isocyanates |

NHS stands for N-hydroxysuccinimide

The functional groups can depend on the type of biomolecule to be immobilized. For example, all proteins contain an amino group on one end and a carboxylate group on the other end, besides all other functional groups provided by the specific amino acids on the sequence. In the case of oligonucleotides these are usually synthesized one nucleotide at a time. Because of this, a single nucleotide label with the desired functional group can be added at some point in the synthesis (usually at the beginning or the end), thus labeling the resulting oligonucleotide. These individual nucleotides can be modified either chemically or enzymatically with any type of functional group in order to provide the desired label. This chemical or enzymatic labeling can be extended to DNA molecules, with the difference that all bases within the molecule targeted by the labeling reaction will be modified. If the desired result is to label the DNA molecule only at one point, the best approach is polymerase chain reaction (PCR) amplification using primers that have been already modified with the desired functional group.

After immobilizing the desired target molecule and performing the desired biochemical application, the molecule can be recovered and the surface regenerated. This can be done by a procedure known as elution. A very common mode of elution of specifically bound molecules is the use of competing molecules, which displace the bound molecule. In order to chose a proper displacer it is important to take into account the nature of the specific interaction. Ligands immobilized through soft metal/soft base interactions on soft metal thin films may be recovered through the use of sulfur-containing competing molecules that displace the heterobifunctional spacers. For example, due to the high aqueous solubility of thiodiglycol and because of its thioether functional group, a high elution recovery can be accomplished using a concentrated solution of thiodiglycol. The substrate may then be reused.

The following Examples are provided to illustrate specific embodiments of the invention and should not be interpreted so as to limit the scope of the claims.

EXAMPLE 1

Immobilization of Biotinylated Oligonucleotide on a Platinum Surface

Silicon chips with platinum thin films were manufactured by electron beam evaporation. Prior to use, these surfaces are cleansed by using a mixture of 13% RBS 35 solution (Pierce) and 33% ethanol in deionized water. The chips are washed in this solution by immersing in an ultrasonic bath at 50° C. for 20 minutes. This is followed by rinsing three times in deionized water using an ultrasonic bath at 50° C. for 10 minutes. After rinsing the chips are blow-dried under nitrogen or argon.

For this example the hetrobifunctional spacer arm was succinimidyl-6-(biotinamido)hexanoate. This molecule is commercially available (Pierce Chemical Co.) or can be synthesized using the information available in the literature (Staros, J. V., Biochemistry, 1982, 21(17):3950–3955). This molecule is a derivative of D-biotin containing an $^6$-aminocaproic acid spacer arm, about 30.5 Å in length, attached to the valeric acid side chain of biotin and terminating in an NHS ester. This NHS ester reacts with amine groups in proteins and other molecules to form stable amide bond derivatives. Optimal reaction conditions are at pH 7–9. Amine-containing buffers such as Trizma, which may compete in the acylation reaction should be avoided. This spacer arm molecule is insoluble in aqueous reaction conditions and must be dissolved in organic solvents prior to the addition to the aqueous buffered reaction solution. A stock solution may be prepared in either of the organic solvents N,N-dimethylformamide (DMF) or dimethylsulfoxide ((DMSO). Addition to the aqueous solution should not exceed 10% organic solvent to avoid precipitation. The molar ratio of the spacer arm molecule to a protein should be 2–50:1 with higher levels resulting in higher incorporation yields.

The chips are then immersed in a 2 mM solution succinimidyl-6-(biotinamido)hexanoate in DMF or ethanol for 12 hours at room temperature. The chips are then washed three times in DMF followed by drying under a stream of nitrogen and immediately used for the immobilization step.

The activated chips are submerged in a 10 mg/ml solution of the amino-labeled oligonucleotide in 0.1 M sodium phosphate, 0.15 M NaCl, at a pH of 7.2 for 30–60 minutes at room temperature, or for several hours at 4° C. The chips are then washed three times in the phosphate buffer followed by drying under a stream of nitrogen.

EXAMPLE 2

Immobilization of a Thiol-labeled PCR Product on Gold Surface

Silicon chips with gold thin films were manufactured by electron beam evaporation. Prior to use these surfaces are cleansed by using a mixture of 13% RBS 35 solution (Pierce) and 33% ethanol in deionized water. The chips are washed in this solution by immersing in an ultrasonic bath at 50° C. for 20 minutes. This is followed by rinsing three times in deionized water using an ultrasonic bath at 50° C. for 10 minutes. After rinsing the chips are blow-dried under nitrogen or argon.

For this example the hetrobifunctional spacer arm was dithiobis(succinimidyl-undecanoate). This molecule can be synthesized using the information available in the literature (Wagner, et al., Biophys. J., 1996, 70:2052–2066). The molecule is made up by two molecules each containing a dodecanethiol spacer arm attached to an NHS ester and held together through a disulfide bond. The activation of the soft metal surface has to be done in the presence of a disulfide reductant buffer such as dithiothreitol and dioxane. This breaks the disulfide bond and leads to two heterobifunctional crosslinkers with a NHS ester for binding amino-containing ligands and a thiol group attached to the soft metal surface. The NHS ester reacts with amine groups in proteins and other molecules to form stable amide bond derivatives. Optimal reaction conditions are at pH 7–9. Amine-containing buffers such as Trizma, which may compete in the acylation reaction should be avoided. This spacer arm molecule is insoluble in aqueous reaction conditions and must be dissolved in organic solvents prior to the addition to the aqueous buffered reaction solution.

The activated chips are then immersed in a 1 mM solution of dithio-bis(succinimidylundecanoate) in 1,4-dioxane for 30–60 minutes at room temperature. The chips are then washed three times in 1,4-dioxane followed by drying under a stream of nitrogen and immediately used for the immobilization step.

The activated chips are submerged in a 1 mg/ml solution of the amino-labeled PCR product in 0.1 M sodium phosphate, 0.15 M NaCl, at a pH of 7.2 for 30–60 minutes at room temperature, or for several hours at 4° C. The chips are then washed three times in the phosphate buffer followed by drying under a stream of nitrogen.

EXAMPLE 3

Immobilization of Antibodies on a Silver Surface

Silicon chips with silver thin films were manufactured by electron beam evaporation. Prior to use these surfaces are cleansed by using a mixture of 13% RBS 35 solution (Pierce) and 33% ethanol in deionized water. The chips are washed in this solution by immersing in an ultrasonic bath at 50° C. for 20 minutes. This is followed by rinsing three times in deionized water using an ultrasonic bath at 50° C. for 10 minutes. After rinsing the chips are blow-dried under nitrogen or argon.

Succinimidyl-6-[6-(((iodoacetyl)amino)-hexanoyl) amino]hexanoate) is a heterobifunctional spacer that contains an NHS ester on one end separated by two aminohexanoate groups from a iodoacetyl group on the other. This molecule is commercially available (Molecular Probes) or can be synthesized using the information available in the literature (Brinkley, M., *Bioconjugate Chem.*, 1992, 3:2–18). The NHS ester reacts with primary amines in different biomolecules to form stable amide bonds. Even though the iodoacetyl group is highly reactive towards soft metals it also reacts with sulfhydryl groups forming a thioether linkage. Another concern with the iodoacetyl groups is that it can be degraded to iodine with light, thus reducing its reactivity. This crosslinker is highly hydrophobic so it must be dissolved in an organic solvent (DMSO or DMF) before adding to the aqueous reaction buffer. Conjugations done with this crosslinker should avoid buffer components containing amines (e.g., Tris, glycine, or imidazole) or sulfhydryls (e.g., dithiothreitol, 2-mercaptoethanol, or cysteine), since these will compete with the desired crosslinking reaction.

The chips are then immersed in a solution containing 2 mM succinimidyl-6-[6-(((iodoacetyl)amino)-hexanoyl) amino]hexanoate) in DMSO for 12 hours at room temperature. The chips are then washed three times in DMSO followed by drying under a stream of nitrogen and immediately used for the immobilization step.

The activated chips are submerged in a 10 mg/ml solution of the antibody in 50 mM sodium borate, 5 mM EDTA, at a pH of 8.3 for 30–60 minutes at room temperature, or for several hours at 4° C. The chips are then washed three times in the borate buffer followed by drying under a stream of nitrogen.

EXAMPLE 4

Recovery of Antibodies Immobilized on a Silver Surface Through the Use of Thiodiglycol as a Displacing Agent Antibodies immobilized through soft metal/soft base interactions on silicon chips with silver thin films can be recovered through the use of sulfur-containing competing molecules to displace the heterobifunctional spacers with an iodine functionality.

In order to chose a proper displacer it is important to take into account the nature of the specific interaction. In this case, the iodine-silver interaction, as described by the HSAB Principle, requires a soft base that can compete for the binding to the immobilized silver (a soft acid). Since it is the iodine group in the spacer, which confers this molecule with its soft base nature, it was the strategy to look for other molecules with a soft base functional group.

Thiodiglycol is a perfect candidate due to its high aqueous solubility and because of its thioether functional group. A high elution recovery can be accomplished by immersing the silver chip with the immobilized antibody of EXAMPLE 3 in a 1 M solution of thiodiglycol in a ultrasonic bath for 1 hour at room temperature. The substrate can then be reused by washing with (50:50) deionized water/ethanol solution in a ultrasonic bath at 50° C. for 20 minutes, followed by heating in an oven for 30 minutes at 100° C. under a partial vacuum in order to drive off the relatively volatile thiodiglycol.

The following claims are presented to specifically point out and distinctly claim the invention. All documents mentioned in this disclosure are incorporated herein by reference.

What is claimed is:

1. A ligand-binding solid surface comprising:
   a) a soft metal solid support and
   b) a heterobifunctional spacer having two functional groups, one of said functional groups comprising a reactive terminal moiety configured to bind a ligand, and one of said functional groups comprising a soft base, said spacer being non-covalently chemi- or physisorbed to said soft metal solid support via soft metal-soft base bonding wherein the soft base is selected from the group consisting of succinimidyl-6-(biotinamido) hexanoate and succinimidyl 6-[6-(((iodoacetyl)amino)-hexanoyl)amino]hexanoate.

2. A ligand-binding solid surface of claim 1 in which the soft metal solid support is selected from the group consisting of silver, copper, gold, platinum (II), mercury, mercury (II), thallium, cadmium (II), platinum (IV) and palladium (II) covered surfaces.

3. A ligand-binding solid surface of claim 1 in which the heterobifunctional spacer comprises a hydrocarbon having a chain length of about 10 to about 40 carbon atoms.

4. A ligand-binding solid surface of claim 1 wherein the heterobifunctional spacer comprises succinimidyl-6-(biotinamido)hexanoate.

5. An assay system comprising a plurality of ligand-binding solid surfaces of claim 1.

6. A method for detecting the presence of a biological molecule comprising exposing a sample containing biological molecules to a ligand-binding solid surface of claim 1.

7. A ligand-binding solid surface of claim 1 wherein said reactive terminal moiety comprises an oligonucleotide linked to said heterobifunctional spacer.

8. A ligand-binding solid surface of claim 1 in which the heterobifunctional spacer comprises succinimidyl 6-[6-(((iodoacetyl)amino)-hexanoyl)amino]hexanoate.

9. A method for preparing a ligand-binding solid surface, comprising:
   a) selecting a soft metal solid support; and
   b) non-covalently immobilizing a heterobifunctional spacer on said solid support via soft metal-soft base bonding, said spacer having two functional groups, one of said functional groups comprising a reactive terminal moiety configured to bind a ligand, and one of said functional groups comprising a soft base, wherein the soft base is selected from the group consisting of succinimidyl-6-(biotinamido)hexanoate and succinimidyl 6-[6-(((iodoacetyl)amino)-hexanoyl)amino]hexanoate.

10. A method of claim 9 in which the soft metal solid support is selected from the group consisting of silver, copper, gold, platinum (II), mercury, mercury (II), thallium, cadmium (II), platinum (IV) and palladium (II) covered surfaces.

11. A method of claim 9 in which the heterobifunctional spacer comprises a hydrocarbon of about 10 to about 40 atoms in length.

12. A method of claim 9 wherein the heterobifunctional spacer comprises succinimidyl-6-(biotinamido)hexanoate.

13. A method of claim 9 wherein the heterobifunctional spacer comprises succinimidyl 6-[6-(((iodoacetyl)amino)-hexanoyl)amino]hexanoate.

* * * * *